US00PP24366P3

(12) United States Plant Patent
Schoone

(10) Patent No.: US PP24,366 P3
(45) Date of Patent: Apr. 1, 2014

(54) ***PHALAENOPSIS* ORCHID PLANT NAMED 'BRUNELLO'**

(50) Latin Name: ***Phalaenopsis* hybrid**
Varietal Denomination: Brunello

(75) Inventor: René Schoone, Assendelft (NL)

(73) Assignee: Floricultura, Heemskerk (NE)

( * ) Notice: Subject to any disclaimer, the term of this patent is extended or adjusted under 35 U.S.C. 154(b) by 117 days.

(21) Appl. No.: 13/374,270

(22) Filed: Dec. 20, 2011

(65) Prior Publication Data

US 2013/0160173 P1 Jun. 20, 2013

(51) Int. Cl.
*A01H 5/00* (2006.01)

(52) U.S. Cl.
USPC ..... Plt./311

(58) Field of Classification Search
USPC ..... Plt./311
See application file for complete search history.

(56) References Cited

PUBLICATIONS

Printout of Official Gazette (Staatscourant) of Sep. 26, 2011 from Netherlands Plant Breeders' Rights office website showing publication of corresponding Netherlands PBR application No. OPS725 granted Aug. 29, 2011, shown on p. 8 (9 pages). (https://zoek.officielebekendmakingen.nl).

*Primary Examiner* — Howard Locker
(74) *Attorney, Agent, or Firm* — Foley & Lardner LLP

(57) ABSTRACT

A new and distinct *Phalaenopsis* plant named 'Brunello' particularly characterized by flowers which are violet with a little bit of a white mark in the center and some yellow and orange at the labellum; plants which may be propagated economically and uniformly using tissue culture; plants which produce more than one inflorescence; long and sturdy inflorescences; and dark-green foliage.

3 Drawing Sheets

Latin name of the genus and species of the plant claimed: *Phalaenopsis* hybrid.

Variety denomination: 'Brunello'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Brunello'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Brunello' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Brunello' originated from a cross made by the inventor in 1998 in Strengweg, Heemskerk, The Netherlands. The female or seed parent is the *Phalaenopsis* cultivar designated 'Tom Coffey', unpatented. The male or pollen parent is the *Phalaenopsis* cultivar designated 'Pink Twilight', unpatented. The new *Phalaenopsis* 'Brunello' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Brunello', which in combination distinguish this *Phalaenopsis* as a new and distinct cultivar:

1. flowers which are violet with a little bit of a white mark in the center and some orange and yellow in the labellum;
2. plant produces more than one inflorescence;
3. plants may be propagated economically and uniformly using tissue culture;
4. inflorescence is long and sturdy; and
5. dark-green foliage.

In comparison with the parental cultivars of 'Brunello', the female parent 'Tom Coffey' has pink flowers about 10 cm in diameter, and the male parent 'Pink Twilight' has purple/violet colored flowers about 7.5 cm in diameter, whereas the flowers of 'Brunello' are violet about 8.5 cm in diameter.

Presently, there is no commercial cultivar to which 'Brunello' can be meaningfully compared.

BRIEF DESCRIPTION OF THE PHOTOGRAPHS

The accompanying photographs illustrate the overall appearance of the new *Phalaenopsis* 'Brunello' showing the colors as true as is reasonably possible with colored reproductions of this type. Colors in the photographs may differ slightly from the color values cited in the detailed botanical description, which accurately describe the color of 'Brunello'.

DETAILED BOTANICAL DESCRIPTION

Figure 1:
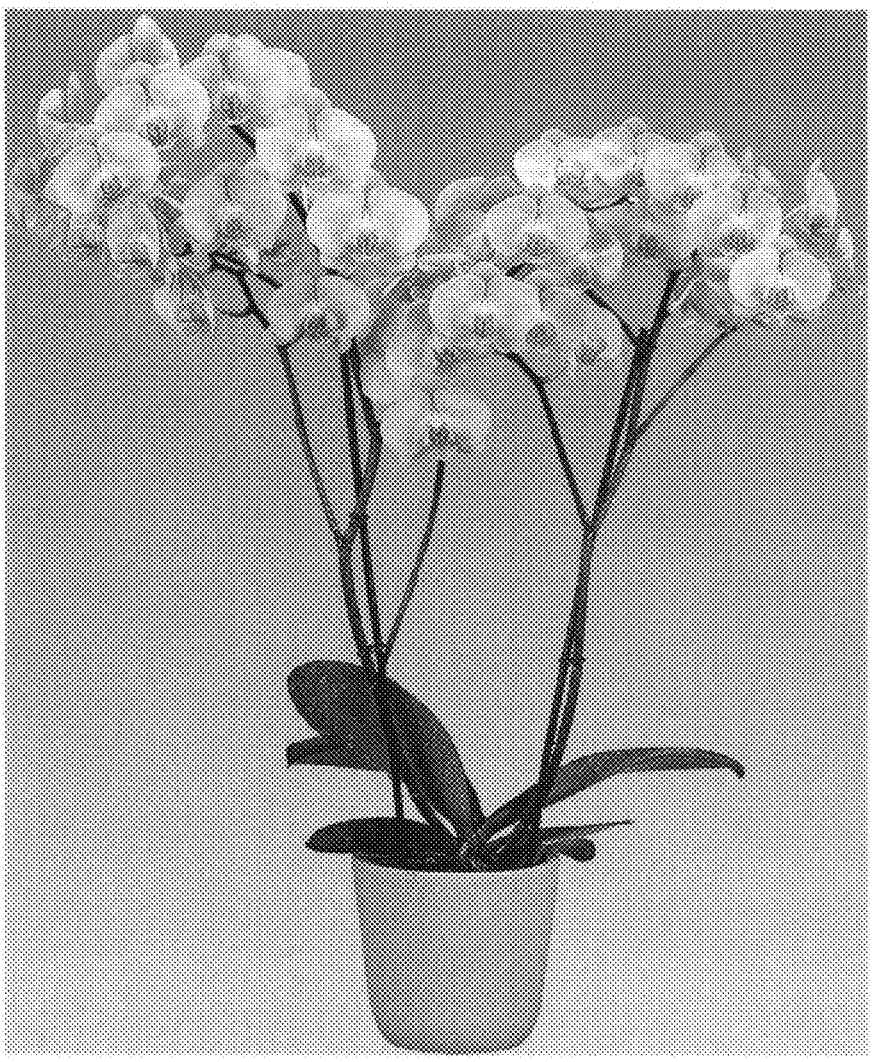
FIG. 1 shows a side view perspective of a typical flowering plant of 'Brunello' in a 12 cm pot, at 16 months of age.

The new *Phalaenopsis* cultivar 'Brunello' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Brunello' as grown in a greenhouse in Strengweg, Heemskerk, The Netherlands, under conditions which closely approximate those generally used in commercial practice. Initially, the ideal temperature to grow plants of 'Brunello' is 27° C. during the day and at night. Then, during the flowering phase of 'Brunello', the ideal growing temperature is 20-22° C. during the day and 18° C. at night. Light levels for growing 'Brunello' are a minimum of 5,000 lux and a maximum of 10,000 lux. A balanced fertilizer with level of 200 ppm N, 87 ppm P, 168 ppm K is applied. Duration of growth of 'Brunello' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Brunello' plants described is 12 months after potting.

Classification:

*Botanical.*—*Phalaenopsis* hybrid.

Parentage:

*Female or seed parent.*—*Phalaenopsis* cultivar designated 'Tom Coffey', unpatented.

*Male or pollen parent.*—*Phalaenopsis* cultivar designated 'Pink Twilight', unpatented.

Propagation:

*Type.*—Tissue culture.

*Rooting habit and description.*—Fleshy; approximately 6 mm-9 mm wide and green/greyed-green in color (RHS 137B and RHS 198A); freely branching. It takes 12 weeks for plants growing in tissue culture to initiate roots.

Plant:

*Size at maturity.*—Height: about 73 cm. Spread: about 65 cm to 70 cm.

*Growth habit.*—Standard; green (RHS 137B) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Alternate; clasping.

*Overall shape of leaf.*—Oval, the tip is blunt and asymmetric.

*Texture.*—Smooth and leathery.

*Pubescence.*—None.

*Mature leaf length.*—About 17 to 18 cm.

*Mature leaf width.*—About 9 cm.

*Mature leaf thickness.*—About 2 mm.

*Mature leaf color.*—Upper side: green RHS 137B. Under side: yellow-green (RHS 144A) and purple (RHS N77A).

*Venation.*—Pattern: parallel. Color of midvein: upper side: green (RHS 137B) and some purple (RHS N77A). under side: yellow-green RHS 144A with some purple RHS N77A.

*Leaf base.*—Acute.

*Margin.*—Entire.

Raceme:

*Quantity per plant.*—About 1 to 2.

*Number of flowers per raceme.*—About 10 to 15.

*Length.*—About 70 to 80 cm.

*Diameter.*—About 8 mm.

*Strength.*—Strong.

*Aspect.*—Upright.

*Texture.*—Glabrous and smooth.

*Color.*—Brown (RHS N200A) with green spots (RHS 139D).

*Internode.*—Length: about 40 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 20 mm to 25 mm. Diameter (at midpoint): about 15 mm to 20 mm. Shape: egg-shaped. Color: purple (RHS N77B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
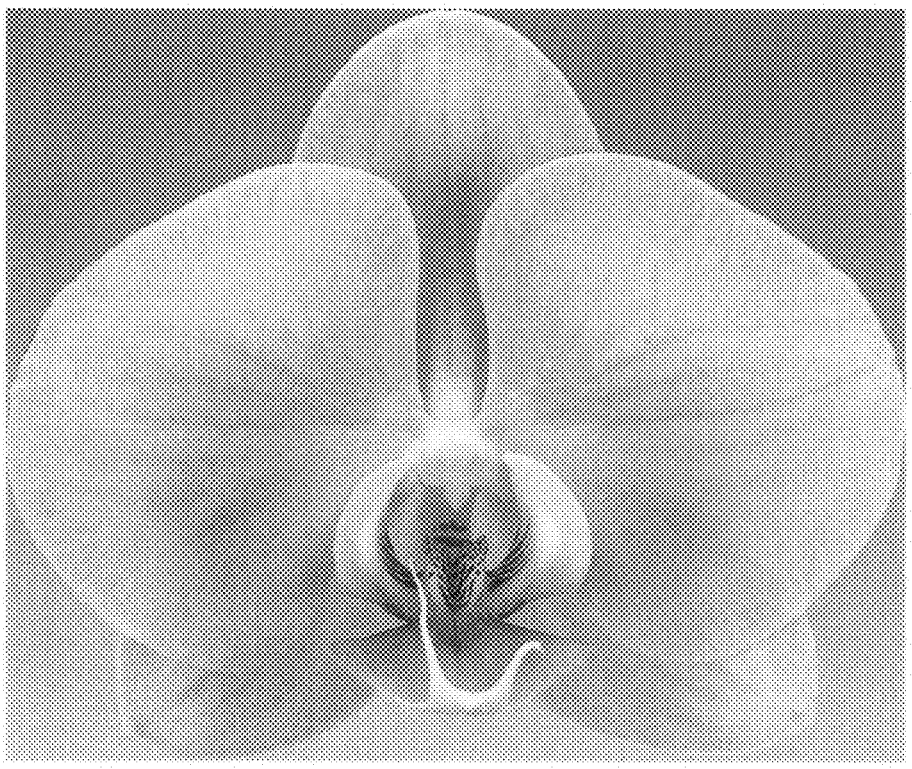
FIG. 2 shows a close-up view of the typical flowers of 'Brunello'.
Figure 3:
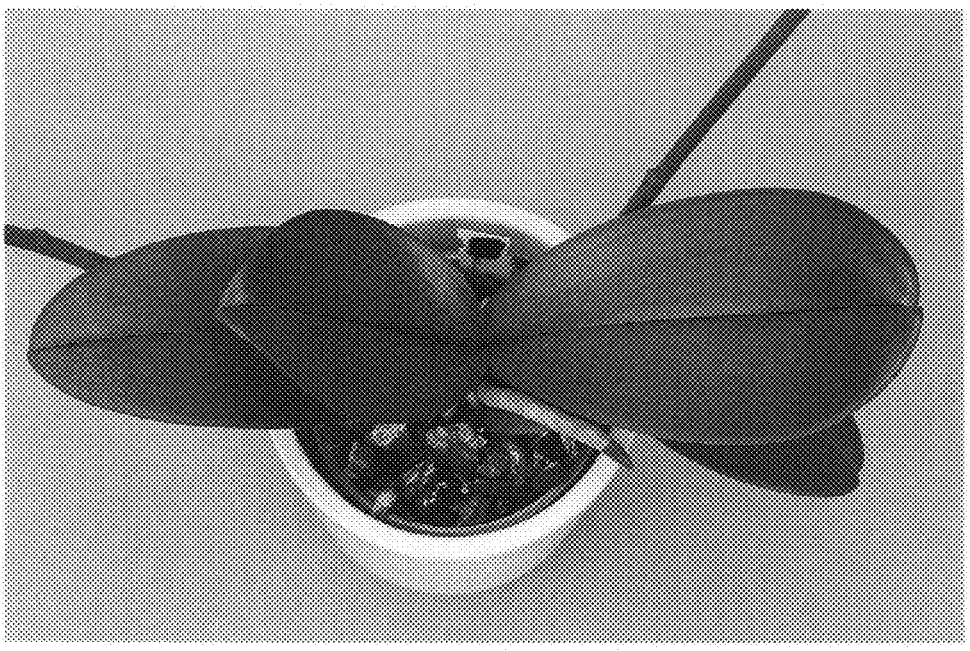
FIG. 3 shows a close-up view of the typical leaves of 'Brunello'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 65 mm. Diameter: about 85 mm. Depth of tube: about 15 mm.

*Petals.*—Quantity and arrangement: six petals and sepals that are trimerous, overlapping and arranged in 2 whorls. Petals are more pronounced than sepals. Arrangement: Whorl of 3 petals, 2 lateral petals and labellum. 2 lateral petals: Overall shape: broadly ovate and weakly cupped. Apex: oval. Margin: weakly undulate. Base: broadly ovate. Length: about 50 mm. Width: about 35 to 40 mm. Texture: Upper surface: smooth and satiny. Under surface: smooth and satiny. Color (when fully opened): upper side: Main color is violet (RHS 84C), with a little bit of a white (RHS NN155C) mark in the center. Under side: Violet (RHS 84C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length: about 15 mm. Width (not flattened): about 22 mm. Texture: Upper & under surface: smooth and satiny. Color (when fully opened): Upper surface: Midlobe: Main color is violet (RHS 84B). The corners and the upper edges are greyed/orange (RHS 172B). At the base in the center is some yellow (RHS 12A) and red/purple stripes/spots (RHS 64A). Lateral lobes: the main color is violet (RHS 84C) with a bit of a white mark at the center (RHS N155C). At the base there are red horizontal stripes (RHS 64A). The bottom edges are greyed-orange (RHS 172A). Under surface: Midlobe: main color is purple (RHS N78C). Upper edges are greyed/orange (RHS 172A). Lateral lobes: purple (RHS N78D & RHS N78C). Upper edge some white (RHS N155C). At the base some purple (RHS N78A) and lower edge some greyed/orange (RHS 172A). Cirrhi: about 19 mm. color: violet (RHS 84C). Pestle (Callosities): Length: about 4 mm. Width (not flattened): about 5 mm. Color: yellow (RHS 12A) with red-purple spots (RHS 64A). On the sides some white (RHS N155C). Pedicel: Length: about 40 mm to 45 mm. Diameter: about 3 mm. Texture: smooth and glabrous. Color: yellow/green (RHS 145D). Closer to the flower a red/purple haze (RHS N74D) and closer to the raceme green (RHS 137C).

*Sepals.*—Arrangement: Whorl of 3 sepals. Overall shape: elliptical and weakly cupped. Length: about 34 mm. Width: about 25 mm to 30 mm. Apex: oval; Lateral sepals are little pointy. Texture: Upper & under surface: smooth and satiny. Color (when fully opened): Upper surface: main color is violet (RHS 84B). Under surface: red/purple (RHS N74C).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 10 mm. Diameter: about 6 mm. Color: violet RHS 84B.

*Pollinia.*—Quantity: Two. Size: about 1 mm. Color: yellow-orange RHS 17A.

*Ovary.*—Length: about 5 mm. Diameter: about 6 mm. Color: white RHS NN155C.

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Brunello', as illustrated and described herein.

* * * * *